(12) United States Patent
Shimoe et al.

(10) Patent No.: US 6,461,338 B1
(45) Date of Patent: Oct. 8, 2002

(54) DISPOSABLE DIAPER

(75) Inventors: Nariaki Shimoe; Yoshikazu Jitoe, both of Kagawa (JP)

(73) Assignee: Uni-Charm Corporation, Ehime (JP)

( * ) Notice: Subject to any disclaimer, the term of this patent is extended or adjusted under 35 U.S.C. 154(b) by 181 days.

(21) Appl. No.: 09/602,118

(22) Filed: Jun. 23, 2000

(30) Foreign Application Priority Data

Jun. 28, 1999 (JP) ............................................ 11-181225
Jul. 15, 1999 (JP) ............................................ 11-201510

(51) Int. Cl.[7] ................................................ A61F 13/15
(52) U.S. Cl. ............................ 604/385.01; 604/385.04; 604/385.101
(58) Field of Search ................................ 604/317–355, 604/358–385.16, 385.25–402

(56) References Cited

U.S. PATENT DOCUMENTS 6,193,701 B1 * 2/2001 Van Gompel et al. ... 604/385.1
6,293,935 B1 * 9/2001 Kimura et al. .............. 604/387
6,326,525 B1 * 12/2001 Hamajima et al. .......... 604/378

* cited by examiner

Primary Examiner—Jeanette Chapman
(74) Attorney, Agent, or Firm—Darby & Darby

(57) ABSTRACT

There is disclosed a disposable diaper having a body including a front face portion to be applied to the abdomen of a wearer; an intermediate portion to be applied to the crotch; and a back face portion to be applied to the back, in which a longitudinal direction is taken from the front face portion to the back face portion of the body, and a transverse direction is taken in a direction perpendicular to the longitudinal direction. The diaper includes a top sheet to be directed toward a liquid receiving side; an outer sheet; and an absorbent core sandwiched between the top sheet and the outer sheet. The top sheet is liquid-permeable at least in a portion for covering a transverse center of the absorbent core and is jointed on two transverse sides directly or indirectly to the outer sheet. In a region containing at least a longitudinal center of the intermediate portion, joint boundaries between the top sheet and the outer sheet enter farther the transverse center side than two transverse side ends of the absorbent core.

17 Claims, 8 Drawing Sheets

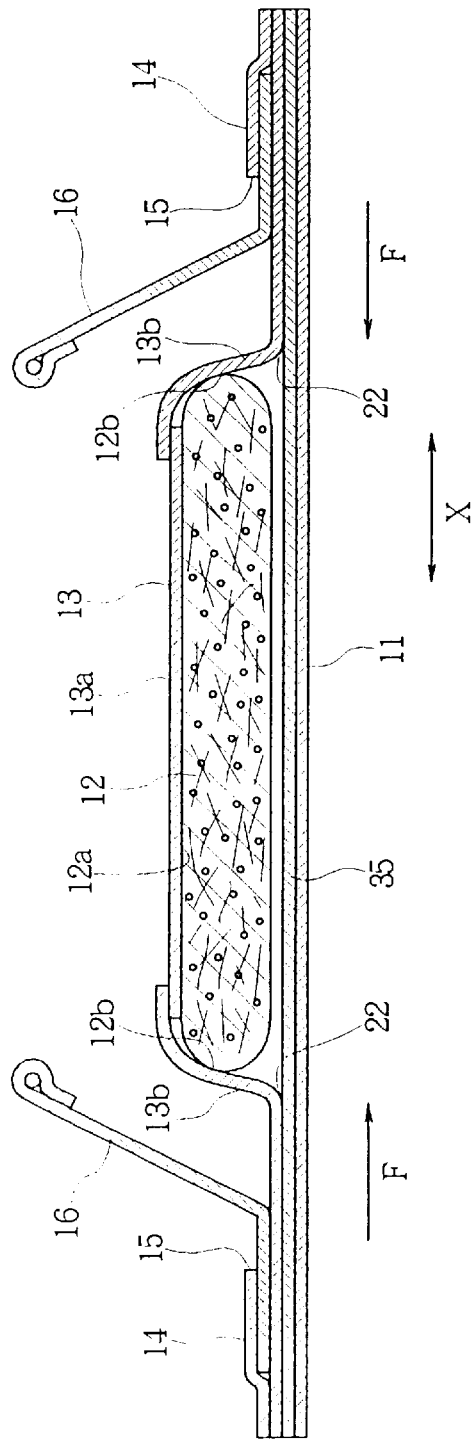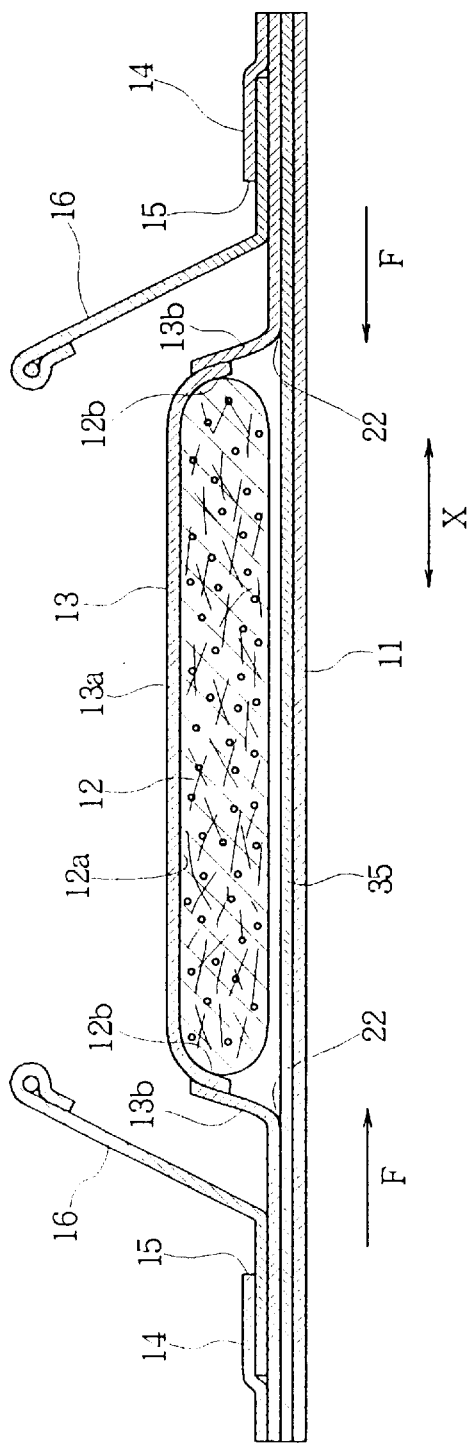

DISPOSABLE DIAPER

BACKGROUND OF THE INVENTION

1. Field of the Invention

The present invention relates to a disposable diaper of an underpants type or an open type and, more particularly, to a disposable diaper which enables securely holding of an absorbent core by a top sheet.

2. Description of the Related Art

FIG. 10 is a sectional view of such a portion of the underpants or open type diaper of the related art as to be applied to a crotch.

As shown in FIG. 10, a disposable diaper 100 of this kind includes: a liquid-permeable top sheet 101 to be directed to the side of a wearer (or a liquid receiving side); and a liquid-impermeable outer sheet 102 to be directed outward. The top sheet 101 and the outer sheet 102 are bonded to each other at two transverse side regions 100a and 100a of the diaper. In a transverse center region 100b, on the other hand, there is sandwiched between the aforementioned top sheet 101 and outer sheet 102 an absorbent core 103 which is made mainly of a fibrous material such as pulp and contains a highly absorbent resin.

In a process of the related art for manufacturing the disposable diaper of this kind, the absorbent core 103 is placed on the outer sheet 102 developed in a planar shape and is then overlaid by the top sheet 101 which is also developed in a planar shape. At this time, in the related art, the adhesion of the top sheet 101 is limited such that the top sheet 101 is adhered to the outer sheet 102 in the aforementioned two side regions 100a and 100a and to an upper surface 103a of the absorbent core 103 in a rising upper face 100c on the liquid receiving side.

In the related art, more specifically, the top sheet 101 is adhered only by pressing it vertically. As a result, the top sheet 101 is adhered only at the horizontal face such as the aforementioned two side regions 100a or rising upper face 100c but not at the non-horizontal face such as two side ends 103c of the absorbent core 103.

Thus, the two side ends 103c of the absorbent core 103 and the top sheet 101 are not adhered, but the absorbent core 103 has a thickness. As a result, spaces 104 and 104 are easily formed between the two side ends 103c and 103c of the absorbent core 103 and the top sheet 101.

In the disposable diaper of the related art, as shown in FIG. 10, the two side ends 103c and 103c of the absorbent core 103 and the top sheet 101 are not adhered, but the spaces 104 and 104 are formed between the two side ends 103c and 103c and the top sheet 101. As a result, the absorbent core 103 is insufficiently held by the top sheet 101. The holding force of the absorbent core 103 is weakened especially in the transverse direction, i.e., leftward or rightward of FIG. 10.

If the wearer moves while wearing the disposable diaper, a twisting force, a transverse offsetting force and a kinking force act on the absorbent core 103. Especially for the underpants type diaper, the wearer walks or crawls while wearing the disposable diaper so that the aforementioned forces to be applied to the aforementioned absorbent core 103 increase.

If the aforementioned forces continuously act, the absorbent core 103 will be twisted or offset at the aforementioned center region 100b of the diaper. As a result, the spaces 104 and 104 between the two side ends 103c and 103c of the absorbent core 103 and the top sheet 101 will easily spread.

If the absorbent core 103 is kinked leftward or rightward, moreover, the upper surface 103a of the absorbent core 103 wrinkles to separate the adhesion between the upper surface 103a of the absorbent core 103 and the top sheet 101, thereby to cause a clearance between the upper surface 103a and the top sheet 101.

If the spaces 104 spread or if the clearance is caused between the upper surface 103a and the top sheet 101, as described above, the liquid such as urine fed to the top sheet 101 cannot be efficiently absorbed by the absorbent core 103 to cause the transverse leakage of urine in the diaper.

SUMMARY OF THE INVENTION

The invention has an object to provide a disposable diaper which is hardly experienced by a twist, offset or kink of an absorbent core in the diaper by stabilizing the holding, i.e., the transverse holding of the absorbent core by a top sheet, so that the absorbing function of the absorbent core can be prevented from any reduction.

According to a first aspect of the invention, there is provided a disposable diaper having a body including a front face portion to be applied to the abdomen of a wearer; an intermediate portion to be applied to the crotch; and a back face portion to be applied to the back, in which a longitudinal direction is taken from the front face portion to the back face portion of the body, and a transverse direction is taken in a direction perpendicular to the longitudinal direction, which comprises a top sheet to be directed toward a liquid receiving side; an outer sheet; and an absorbent core sandwiched between the top sheet and the outer sheet, the top sheet being liquid-permeable at least in a portion for covering a transverse center of the absorbent core and being jointed on two transverse sides directly or indirectly to the outer sheet, wherein, in a region containing at least a longitudinal center of the intermediate portion, joint boundaries between the top sheet and the outer sheet enter farther the transverse center side than two transverse side ends of the absorbent core.

Here, the aforementioned top sheet and outer sheet may be adhered and jointed directly to each other or through another sheet. On the other hand, the top sheet may be made liquid-permeable in its portion covering at least the absorbent core.

In the diaper according to the first aspect of the invention, the top sheet is in contact with not only the liquid receiving side surface of the absorbent core but also the two transverse side ends of the absorbent core, and enters the two end portions of the back side of the absorbent core. As a result, the absorbent core can be wrapped and restricted from the two transverse sides by the top sheet so that the absorbent core is hardly twisted, offset and kinked.

Here, the top sheet may include a liquid-permeable sheet and side sheets directly or indirectly jointed to the liquid-permeable sheet on two transverse sides thereof, and joint boundaries between the side sheets and the outer sheet may enter farther the transverse center side than the two transverse side ends of the absorbent core.

Here, it is preferable that in the region containing at least the longitudinal center of the intermediate portion, the top sheet is jointed to the two transverse side ends of the absorbent core.

On the other hand, the liquid receiving side surface of the absorbent core and the top sheet are usually adhered to each other. When the back side of the absorbent core and the outer sheet are adhered, moreover, the absorbent core can be reliably held on the diaper.

In the diaper according to the first aspect of the invention, the aforementioned top sheet and the outer sheet may be jointed at the two transverse sides after the top sheet was so pressed or shaped as to wrap the absorbent core from the upper surface to the two side ends thereof.

However, if in the region containing at least the longitudinal center of the intermediate portion, there is disposed elasticity applying means for bringing the joint boundaries closer to the transverse center, it is easy to form a structure in which the two side ends of the absorbent core are wrapped by the top sheet.

In this case, it is preferable that the top sheet is not elastically shrunken in the transverse direction, or that the transverse elastic shrinking distortion in the free state of the diaper is made larger at the elasticity applying means than at the top sheet.

By combining such top sheet with the elasticity applying means, the shrinking force of the aforementioned elasticity applying means can be utilized to easily realize a structure in which the two side ends of the absorbent core are wrapped by the top sheet.

According to a second aspect of the invention, on the other hand, there is provided a disposable diaper having a body including a front face portion to be applied to the abdomen of a wearer; an intermediate portion to be applied to the crotch; and a back face portion to be applied to the back, in which a longitudinal direction is taken from the front face portion to the back face portion of the body, and a transverse direction is taken in a direction perpendicular to the longitudinal direction, which comprises a top sheet to be directed toward a liquid receiving side; an outer sheet; and an absorbent core sandwiched between the top sheet and the outer sheet, the top sheet being liquid-permeable at least in a portion for covering a transverse center of the absorbent core and being jointed on two transverse sides directly or indirectly to the outer sheet, wherein, in a region containing at least a longitudinal center of the intermediate portion, there is disposed elasticity applying means for bringing joint boundaries between the top sheet and the outer sheet closer to the transverse center; wherein the top sheet is not elastically shrunken in the transverse direction, or the transverse elastic shrinking distortion in the free state of the diaper is made larger at the elasticity applying means than at the top sheet; and wherein, in the region containing at least the longitudinal center of the intermediate portion, the top sheet is jointed to two transverse side ends of the absorbent core.

Here, the top sheet may include a liquid-permeable sheet and side sheets directly or indirectly jointed to the liquid-permeable sheet on two transverse sides thereof; the liquid permeable sheet or the side sheets may be not elastically shrunken in the transverse direction, or the transverse elastic shrinking distortion in the free state of the diaper may be made larger at the elasticity applying means than at the liquid-permeable sheet or the side sheets; and in the region containing at least the longitudinal center of the intermediate portion, the liquid-permeable sheet or the side sheets may be jointed to the two transverse side ends of the absorbent core.

The diaper according to the second aspect of the invention is on the premise that there is provided the elasticity applying means for bringing the joint boundaries between the top sheet and the outer sheet to the transverse center, and the aforementioned two transverse side ends of the absorbent core and the aforementioned top sheet are jointed.

By using the elasticity applying means, in the diaper according to the second aspect of the invention, the two side ends of the absorbent core can be reliably wrapped by the top sheet. Since the two side ends of the absorbent core and the top sheet are jointed to each other, moreover, the kink of the absorbent core in the diaper or the like is hardly caused.

In the aforementioned structure, the outer sheet may be an elastically shrinking sheet for elastically shrinking in the transverse direction, for example a shrinking nonwoven fabric or shrinking film, etc. and the elastic shrinking force of the outer sheet may be used as the elasticity applying means.

Alternatively, the elasticity applying means may be an elastic member such as a plurality of elastic bands for exhibiting an elastic shrinking force in the transverse direction, and the elastic member may be fixed in a transversely extended state either between the absorbent core and the outer sheet or on the outer face of the outer sheet.

In the diaper according to the first or second aspect of the invention, moreover, it is preferable: that leakage-preventing cuffs are arranged on the liquid receiving side of the body and are extended in the longitudinal direction and spaced apart from each other in the transverse direction, that the leakage-preventing cuffs include: sheets having fixed end portions fixed on the diaper along the longitudinal direction and free end portions; and elastic members attached to the sheets at the free end portions or at their vicinities for exhibiting shrinking forces in the longitudinal direction, and that in the region containing at least the longitudinal center of the intermediate portion, the fixed end portions of the leakage-preventing cuffs are apart from the two transverse side ends of the absorbent core so that the liquid can be absorbed at the two side ends by the absorbent core.

On the other hand, leakage-preventing cuffs may be arranged on the liquid receiving side of the body and may be extended in the longitudinal direction and spaced apart from each other in the transverse direction, the leakage-preventing cuffs may include: sheets having fixed end portions fixed on the body along the longitudinal direction and free end portions; and elastic members attached to the sheets at the free end portions or at their vicinities for exhibiting shrinking forces in the longitudinal direction, and the sheets for forming the leakage-preventing cuffs may be used as the side sheets. The joint boundaries between the side sheets and the outer sheet may enter farther the center side than the two transverse side ends of the absorbent core, or the aforementioned side sheets may be jointed to the two transverse side ends of the absorbent core.

Moreover, the invention is effective for the structure, in which two transverse side portions of the front face portion and two transverse side portions of the back face portion are jointed to each other, in which a waist opening is formed from individual edge portions of the front face portion and the back face portion, and in which leg openings are formed from two side portions of the intermediate portion so that the body has an underpants shape. However, the invention could also be applied to the open type diaper.

BRIEF DESCRIPTION OF THE DRAWINGS

FIG. 6 is a sectional view showing a diaper according to another embodiment of the invention and corresponding to FIG. 4;

FIG. 7 is a sectional view showing a diaper according to another embodiment of the invention and corresponding to FIG. 4;

DESCRIPTION OF THE PREFERRED EMBODIMENTS

Figure 1:
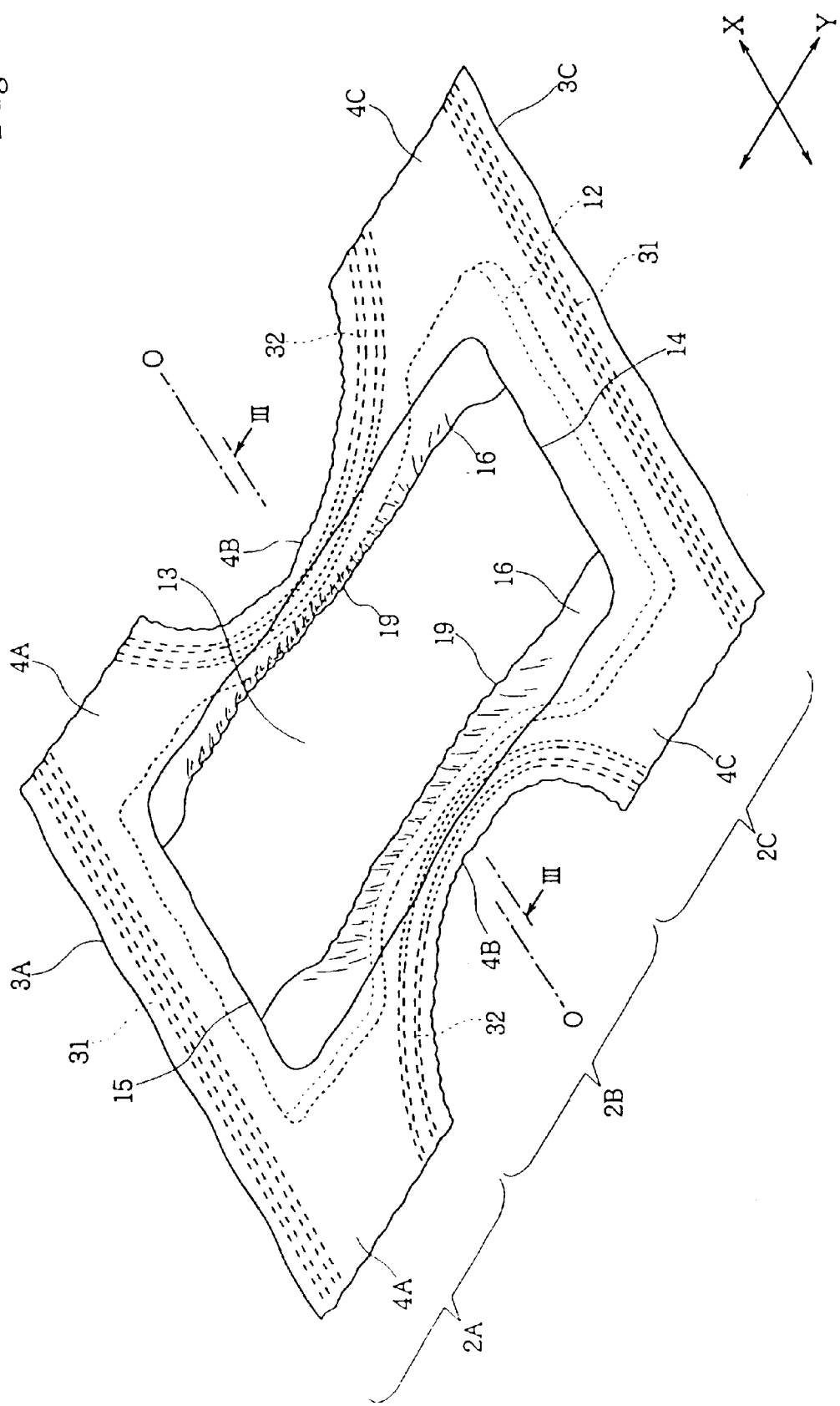
FIG. 1 is a perspective view showing an underpants type diaper in a developed state according to a first embodiment of the invention.
Figure 2:
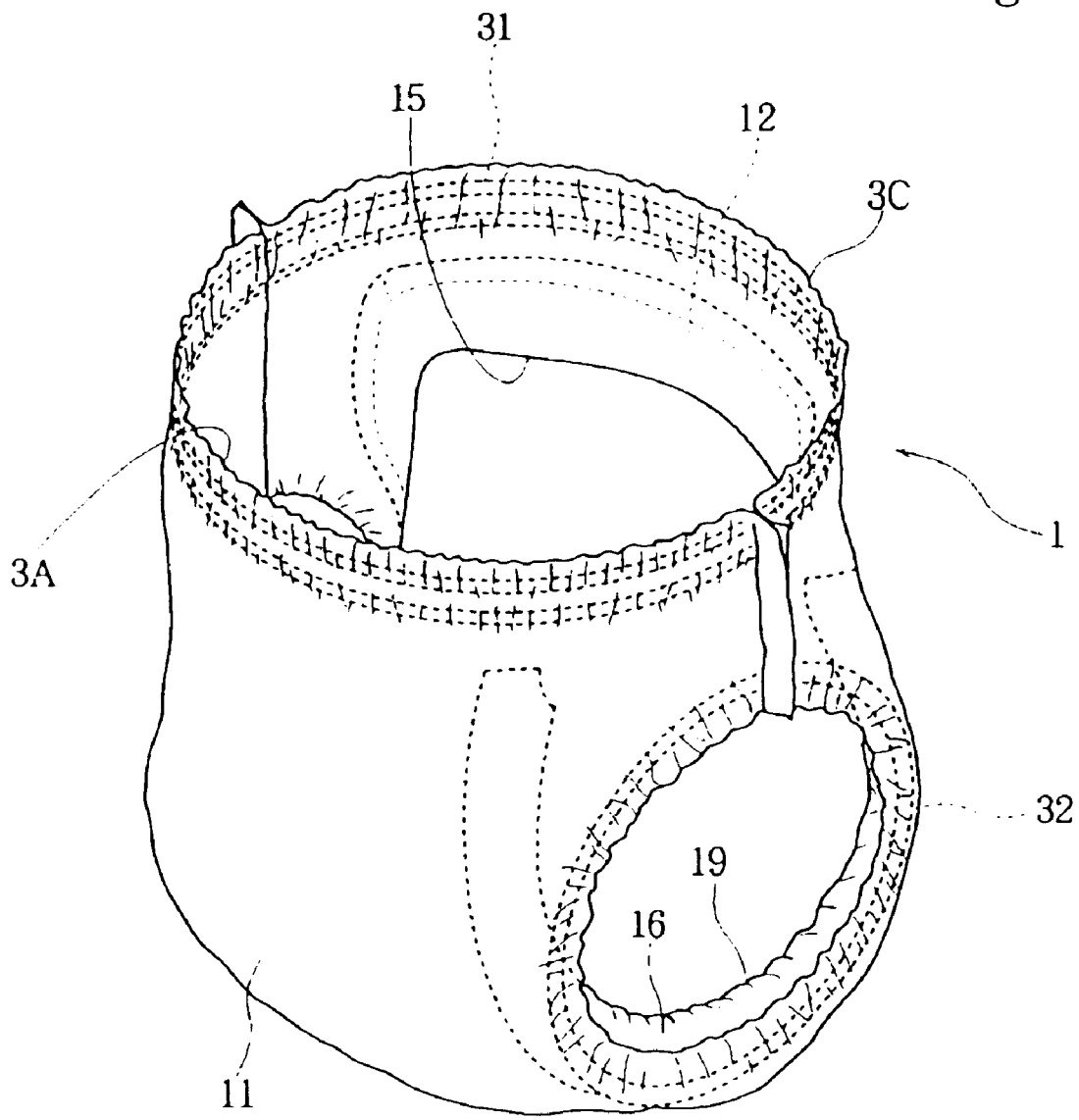
FIG. 2 is a perspective view showing the underpants type diaper according to a first embodiment of the invention.
Figure 3:
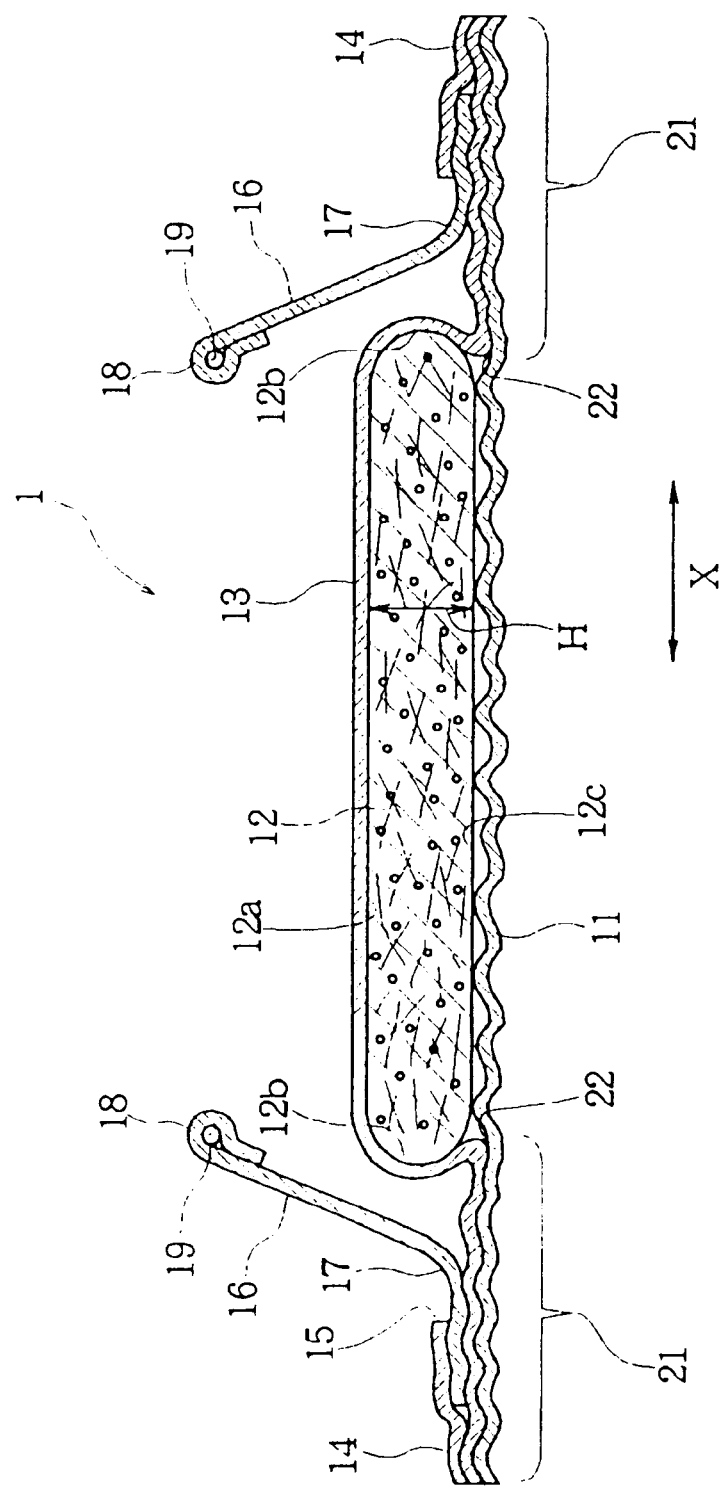
FIG. 3 is a sectional view along line III—III of FIG. 1.
Figure 4:
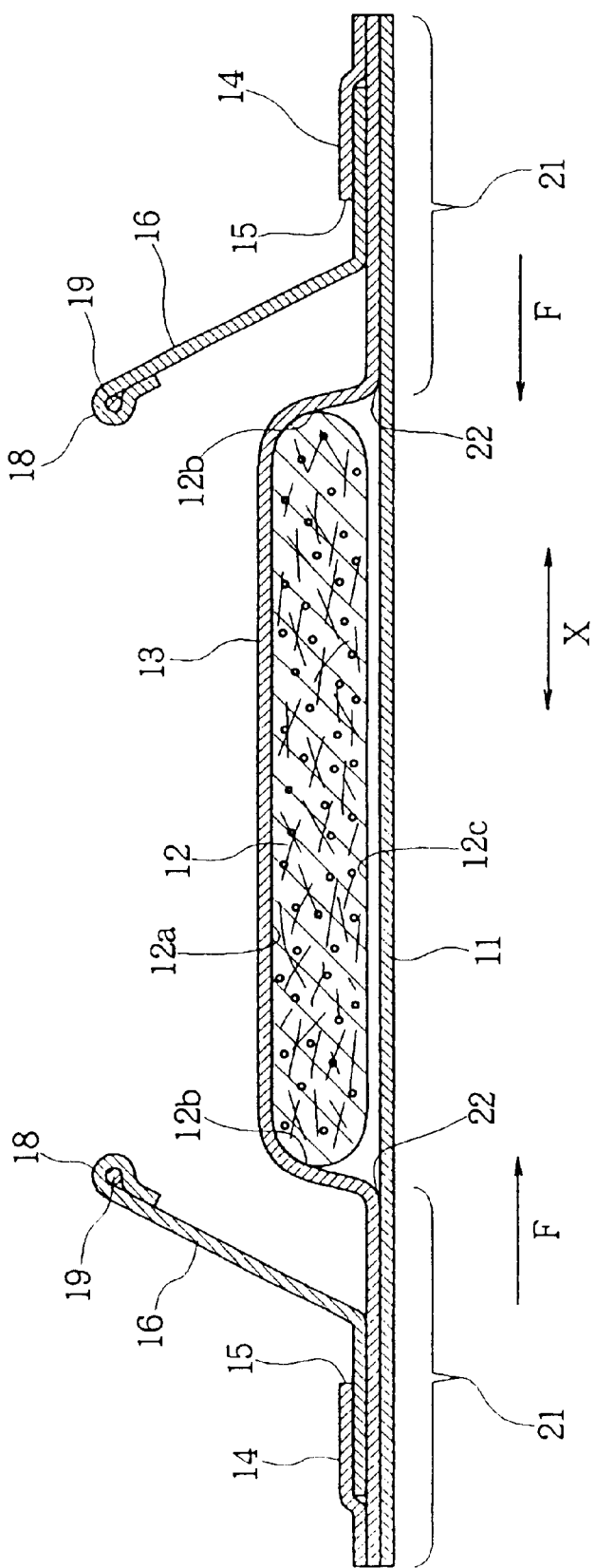
FIG. 4 is a sectional view showing the state in which the diaper of FIG. 3 is transversely extended.
Figure 5:
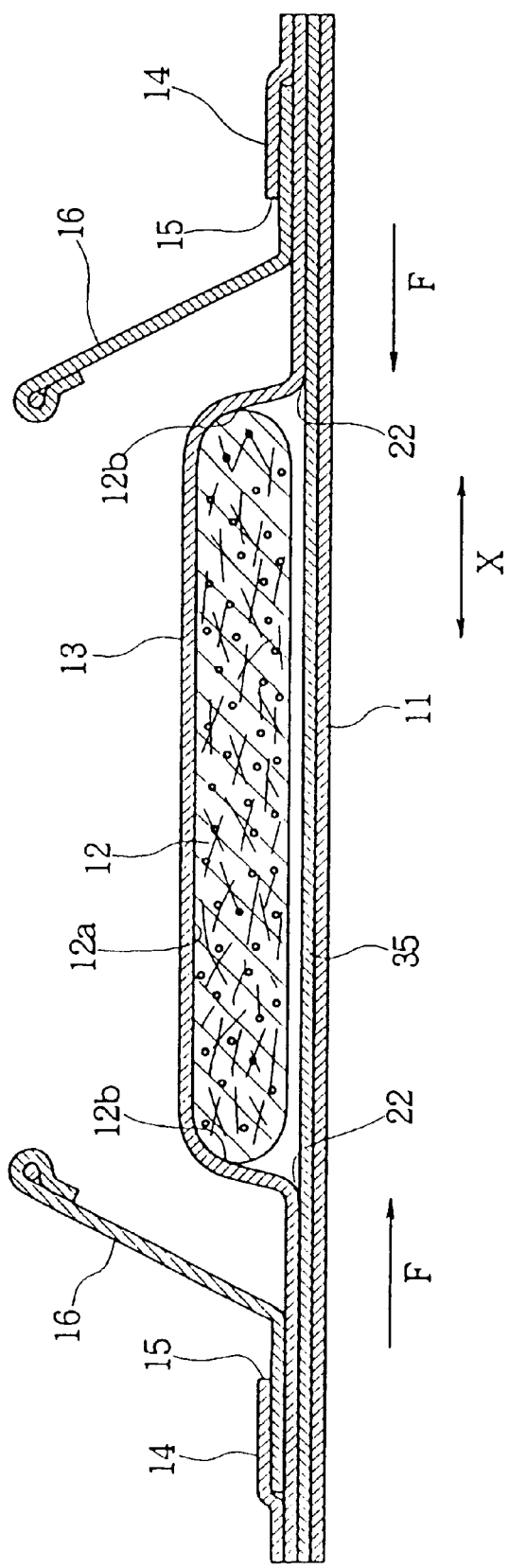
FIG. 5 is a sectional view showing a diaper according to a second embodiment of the invention and corresponding to FIG. 4.

FIG. 1 is a perspective view showing an underpants type disposable diaper according to a first embodiment of the invention in a development from the side of a liquid-permeable sheet; FIG. 2 is a perspective view showing the underpants type disposable diaper shown in FIG. 1; FIG. 3 is a sectional view along line III—III of FIG. 1; FIG. 4 is a sectional view showing a state before elasticity applying means elastically shrinks; and FIG. 5 is a sectional view of a disposable diaper according to a second embodiment of the invention.

A disposable diaper 1, as shown in FIG. 2, is formed in advance into the shape of underpants and is given the so-called "hour glass shape", as shown in FIG. 1, in a developed state before it is shaped. In the developed state shown in FIG. 1, the diaper 1 is constructed to include: a front face portion 2A to be applied to the abdomen of a wearer when the diaper 1 is used; a back face portion 2C to be applied for use to the buttock and/or back; and an intermediate portion 2B to have its two side portions 4B and 4B applied for use to the thigh and to be worn on the crotch. A direction from the front face portion 2A through the intermediate portion 2B to the back face portion 2C is taken in Y-direction (or in a longitudinal direction), and a perpendicular direction is taken in X-direction (or in a transverse direction).

This disposable diaper 1 is made, as shown in a sectional view of FIG. 3, by placing an absorbent core 12 on an outer sheet 11 and by covering the absorbent core 12 with a liquid-permeable top sheet 13. The top sheet 13 is covered with a liquid-impermeable open auxiliary sheet 14 and is exposed to the outside through an open window 15 which opens in the central portion of the open auxiliary sheet 14.

The aforementioned outer sheet 11, top sheet 13 and open auxiliary sheet 14 are all contoured to have an hour glass shape of substantially equal sizes.

The aforementioned outer sheet 11 and top sheet 13 are bonded and jointed to each other in the outer regions of the transverse direction (or the X-direction) and the longitudinal direction (or the Y-direction). For this bonding and jointing treatment, there is used a hot-melt type adhesive, for example. The sectional view of the intermediate portion 2B shown in FIG. 3 designates the joint regions of the outer sheet 11 and the top sheet 13 by 21 and 21. The joint boundaries between the outer sheet 11 and the top sheet 13 are designated by reference numerals 22 and 22. The term "joint boundaries" as used herein is meant to indicate the end portions of the aforementioned joint regions 21 and 21 facing the transverse center of the diaper. The term "transverse center" as used herein is meant to indicate the position midway between two transversely spaced apart sides (i.e., two transverse sides). The term "longitudinal center" as used herein, on the other hand, is meant to indicate the position midway between two longitudinally spaced apart ends (i.e., two longitudinal ends).

When the disposable diaper 1 is in a free state, as shown in FIG. 3, the aforementioned joint boundaries 22 and 22 are located inside of two transverse side ends 12b and 12b of the absorbent core 12. In other words, the joint boundaries 22 and 22 enter farther the transverse center side than the two transverse side ends 12b and 12b. As a result, a liquid receiving side surface 12a of the absorbent core 12 and the two transverse side ends 12b and 12b of the absorbent core 12 are wrapped and held in the top sheet 13.

On the other hand, the surface 12a of the absorbent core 12 and the top sheet 13 are bonded to each other with a hot-melt type adhesive which is applied in a spiral shape or an undulating shape. In the two side ends 12b and 12b of the absorbent core 12, moreover, the absorbent core 12 and the top sheet 13 are adhered with a hot-melt type adhesive.

Here, it is preferable that the top sheet 13 is adhered to the two side ends 12b and 12b of the absorbent core 12 at least over the upper half of the area of the thickness H. However, it is the most preferable that the top sheet 13 is adhered to the two side ends 12b and 12b of the absorbent core 12 substantially all over the area of the thickness H.

On the other hand, the back face 12c of the absorbent core 12 and the outer sheet 11 may be adhered with a hot-melt type adhesive.

It is desired that such a structure as shown in FIG. 3 for the absorbent core 12 to be wrapped by the top sheet 13 is formed all over the longitudinal direction (or the Y-direction) of the disposable diaper 1. It is, however, necessary that the wrapping structure shown in FIG. 3 is made at least in the intermediate portion 2B. If the wrapping structure shown in FIG. 3 is realized within a range of a predetermined longitudinal length containing a longitudinal center O—O of the intermediate portion 2B to be applied to the crotch, more specifically, it is possible to keep the state in which the absorbent core 12 is reliably held in the transverse direction by the top sheet 13, when the motion of the crotch acts on the absorbent core 12.

At least in the intermediate portion 2B, therefore, the absorbent core 12 is hardly twisted, offset or kinked. As a result, any void due to a peeling of the adhesive or the like is hardly made between the side ends 12b of the absorbent core 12 and the top sheet 13 and between the surface 12a of the absorbent core 12 and the top sheet 13, so that the absorbing function of the absorbent core 12 can be sufficiently exhibited. Since the side ends 12b of the absorbent core 12 and the top sheet 13 are in a close contact, on the other hand, a sufficient liquid absorbing function can also be exhibited at the aforementioned side ends 12b.

The aforementioned top sheet 13 is for example, formed of a point bond, air through, spun bond or spun lace nonwoven fabric made of either hydrophobic fibers subjected to a hydrophilic treatment or hydrophilic fibers. These materials have a basis weight (This may be referred to as "METSUKE") of 10 to 40 g/m$^2$. On the other hand, the aforementioned open auxiliary sheet 14 is, for example, formed of either a point bond nonwoven fabric made of hydrophobic fibers or the aforementioned point bond nonwoven fabric subjected to a water-repelling treatment.

In this embodiment, both the aforementioned top sheet 13 and open auxiliary sheet 14 are formed of a nonwoven fabric which is not elastically shrunken in the transverse direction (or the X-direction).

The aforementioned outer sheet 11 is made elastically shrinkable in the transverse direction (or the X-direction). For example, the outer sheet 11 is formed of an extensible nonwoven fabric having an elastically shrinking function such as a point bond, spun bond or spun lace nonwoven fabric containing 80% or more crimped fibers. Alternatively, the outer sheet 11 may be formed of a liquid-impermeable extensible film having an elastically shrinking function and made of a thermoplastic resin of olefin, styrene or urethane groups. In any event, the outer sheet 11 has a basis weight of 10 to 40 $gm/^2$.

When the extensible nonwoven fabric is used for the outer sheet 11, it is preferably subjected to a water-repelling treatment to lower the liquid-permeable function. Alternatively, a water-proof resin film may be sandwiched between the outer sheet formed of the extensible nonwoven fabric and the absorbent core 12. In this case, the resin film may be either extensible or unextensible.

When the liquid-impermeable extensible film having an elastic shrinking function is used for the outer sheet 11, on the other hand, this outer sheet 11 may be used as the outermost sheet of the diaper. Alternatively, a nonwoven fabric may be laminated on the outer side of the extensible film and used as the outermost sheet. In this case, the nonwoven fabric may be either extensible or unextensible.

In short, if the extensible sheet exhibiting the elastic shrinking function is used as the outer sheet 11, another sheet to be laminated on the former may be either extensible or unextensible.

The absorbent core 12 is made of an absorbent material. For example, the absorbent core 12 may be formed by wrapping pulverized pulp or a mixture of pulverized pulp and a highly water-absorbent polymer with an absorbent sheet such as tissues.

In this embodiment, the difference in the elastic shrinking distortion in the X-direction between the outer sheet 11 and the top sheet 13 is utilized to enable the top sheet 13 to wrap the surface 12a and the two side ends 12b and 12b of the absorbent core 12, as shown in FIG. 3. It is, therefore, preferable that the elastic shrinking function is exhibited by the outer sheet 11 but not by the top sheet 13, as has been described hereinbefore.

However, the top sheet 13 may have an extensibility to exhibit the elastic shrinking function in the transverse direction. In this case, it is necessary in the free state of the disposable diaper 1 that the distortion of the top sheet 13 in the transverse direction is smaller than the distortion of the outer sheet 11 due to the elastic shrinkage in the transverse direction. In cases including the case in which the top sheet 13 does not cause the elastic shrinking distortion in the transverse direction, it is preferred that the difference in the free state between the transverse shrinking distortions of the outer sheet 11 and the top sheet 13 is no less than 10% and no more than 30%. If the distortion difference is less than the aforementioned range, the top sheet 13 cannot wrap the absorbent core 12 sufficiently. If the distortion difference exceeds the aforementioned range, the transverse compression to act on the absorbent core 12 may grow so high as to wrinkle.

Here, the distortion is expressed by $(L1=L0)/L0 \times 100(\%)$ if the length of the flat sheet portion when the outer sheet 11 and the top sheet 13 are to be jointed at the aforementioned joint regions 21 and 21 is designated by L0 and if the length of the flat sheet portion after the outer sheet 11 was elastically shrunken, as shown in FIG. 3, is designated by L1.

On the inner sides of the two side portions 4B and 4B of the disposable diaper 1 in the transverse direction (or the X-direction), on the other hand, there are provided leakage-preventing cuffs 16 and 16. These leakage-preventing cuffs 16 and 16 are made of a hydrophobic sheet and are clamped at their root end portions between the top sheet 13 and the open auxiliary sheet 14 and adhered and jointed at their root end portions to the top sheet 13 and the open auxiliary sheet 14, respectively, as shown in FIG. 3.

In FIG. 3, the fixed ends of the leakage-preventing cuffs 16 and 16 are designated by numerals 17 and 17. Within the range of a predetermined length in the longitudinal direction containing the longitudinal center O—O of the intermediate portion 2B, as shown in FIG. 1, the root end portions of the aforementioned leakage-preventing cuffs 16 and 16 are located away from the two transverse side ends 12b and 12b of the aforementioned absorbent core 12. At free ends 18 and 18 of the leakage-preventing cuffs 16 and 16, on the other hand, there are disposed elastic members 19 and 19 for exhibiting elastic shrinking forces in the longitudinal direction (or the Y-direction).

In this disposable diaper 1, as shown in FIG. 3, the top sheet 13 is always in contact with the surface 12a and the two side ends 12b and 12b of the absorbent core 12 so that a body liquid such as urine given to the top sheet 13 is easily transmitted through the top sheet 13 and absorbed from the surface 12a by the absorbent core 12. On the other hand, the body liquid having flown to the two transverse sides is also easily transmitted through the top sheet 13 and absorbed from the two side ends 12b and 12b by the absorbent core 12. In short, the absorbent core 12 has a remarkably widened surface area for absorbing the body liquid. In at least the intermediate portion 2B, on the other hand, the fixed ends 17 and 17 of the leakage-preventing cuffs 16 and 16 are apart from the two side ends 12b and 12b of the absorbent core 12. As a result, the body liquid having flown to the two transverse sides of the diaper arrives between the leakage-preventing cuffs 16 and the side ends 12b of the absorbent core 12 so that it is absorbed from the side ends 12b without being obstructed by the leakage-preventing cuffs 16.

Here will be described a process for manufacturing the aforementioned disposable diaper 1.

As shown in FIG. 4, the outer sheet 11 is elastically extended in the transverse direction (or the X-direction) within a range of 10 to 30%. In this state, the absorbent core 12 is placed at the transverse center portion of the outer sheet 11. At this time, the back face 12c of the absorbent core 12 may and may not be adhered to the outer sheet 11.

Next, the top sheet 13 is placed in a free state, i.e., without being extended in the X-direction on the outer sheet 11 and the absorbent core 12. At this time, the hot-melt type adhesive is applied to the whole area (i.e., the whole length in the transverse direction) of the back face (to confront the absorbent core 12) of the top sheet 13. Moreover, the root end portions of the leakage-preventing cuffs 16 and 16 are placed through the hot-melt type adhesive on the top sheet 13 and are overlaid by the open auxiliary sheet 14 through the hot-melt type adhesive.

At this time, the individual sheets are preferably pressed vertically at the joint regions 21 and 21. On the other hand, the top sheet 13 may be lightly pressed downward on the surface 12a of the absorbent core 12.

When the extending force of the outer sheet 11 in the X-direction is eliminated after the aforementioned adhesive applying step and laminating step, the outer sheet 11 elastically shrinks in F-direction toward the transverse center. At this time, the joint boundaries 22 and 22 between the outer sheet 11 and the top sheet 13 approach toward the transverse center. As a result, the aforementioned joint boundaries 22 and 22 go farther toward the center than the two side ends 12b and 12b of the absorbent core 12, as shown in FIG. 3. By the aforementioned shrinking force of the outer sheet 11, on the other hand, the top sheet 13 is pushed onto the two side ends 12b and 12b of the absorbent core 12 so that the aforementioned two side ends 12b and 12b and the top sheet 13 are adhered to each other by the adhesive which has been applied to the back face of the top sheet 13.

Next, transverse side portions 4A of the front face portion 2A and transverse side portions 4C of the back face portion 2C are jointed to each other to form a waist opening with the individual edge portions, i.e., waist end portions 3A and 3C of the front face portion 2A and the back face portion 2C. Moreover, leg openings are individually formed at the two side portions 4B of the intermediate portion 2B to form the underpants type disposable diaper, as shown in FIG. 2.

Here in the embodiment shown in FIGS. 1 and 2, elastic members (or elastic bands) 31 are transversely attached to the aforementioned waist end portions 3A and 3C so that waist gathers are formed at the waist openings by the elastic shrinking forces of the aforementioned elastic members 31, as shown in FIG. 2. Elastic members (or elastic bands) 32 on the leg side are attached to the aforementioned two side portions 4B so that leg gathers (or cuffs on the leg sides) are formed around the leg openings by the elastic shrinking forces of the aforementioned elastic members 32, as shown in FIG. 2. Moreover, the aforementioned leakage-preventing cuffs 16 and 16 rise toward the wearer on the inner sides of the aforementioned leg openings.

Next, FIG. 5 is a sectional view showing a disposable diaper according to a second embodiment of the invention in such a transversely extended state as in FIG. 4.

In the embodiment shown in FIG. 5, the outer sheet 11 is made of a nonwoven fabric or a water-proof resin film having no elastic shrinking function or a small elastic shrinkage factor. Between the top sheet 13 and the outer sheet 11, however, there are sandwiched elastic members 35 which exhibit elastic shrinking forces in the X-direction. These elastic members 35 are exemplified by transversely extending elastic bands and are longitudinally arranged in plurality within a range of a predetermined length in the longitudinal direction (or the Y-direction) containing the center O—O of the intermediate portion 2B shown in FIG. 1. These elastic members 35 are adhered throughout their lengths to the outer sheet 11 while being transversely extended by 10 to 30%.

In FIG. 5, the aforementioned elastic members 35 are jointed to the outer sheet 11 while being extended in the X-direction by about 10 to 30%. If the elastic members 35 are set free, therefore, the outer sheet 11 elastically shrinks toward the transverse center, and the joint boundaries 22 and 22 move farther toward the transverse center than the two side ends 12b and 12b of the absorbent core 12 so that the absorbent core 12 is wrapped with the top sheet 13, as in FIG. 3.

Here, in the foregoing embodiment, the top sheet 13 is formed of one sheet such as of liquid-permeable nonwoven fabric and placed on the upper faces of the outer sheet 11 and the absorbent core 12. However, the top sheet 13 may be so treated that the portion covering the upper surface 12a of the absorbent core 12 may be liquid-permeable whereas the portions covering the two transverse side portions (i.e., the two side ends 12b and 12b) may be hydrophobic and liquid-impermeable.

In another embodiment of the invention of FIG. 6, the top sheet 13 is formed of a liquid-permeable sheet 13a covering the absorbent core 12 and side sheets 13b jointed to the two sides of the former sheet 13a in the transverse direction (or the X-direction). These side sheets 13b may be either liquid-permeable or liquid-impermeable. In this case, as the diaper elastically shrinks, as shown in FIG. 3, the joint boundaries 22 and 22 between the aforementioned side sheets 13b and outer sheet 11 enter farther the center side than the two side ends 12b and 12b of the absorbent core 12. Moreover, the aforementioned side sheets 13b are bonded and jointed to the two side ends 12b and 12b of the aforementioned absorbent core 12. Alternatively, the liquid-permeable sheet 13a may be bonded and jointed to the two side ends 12b and 12b of the absorbent core 12 as shown in FIG. 7. Here, the side sheets 13b may be the open auxiliary sheets 14.

Figure 8:
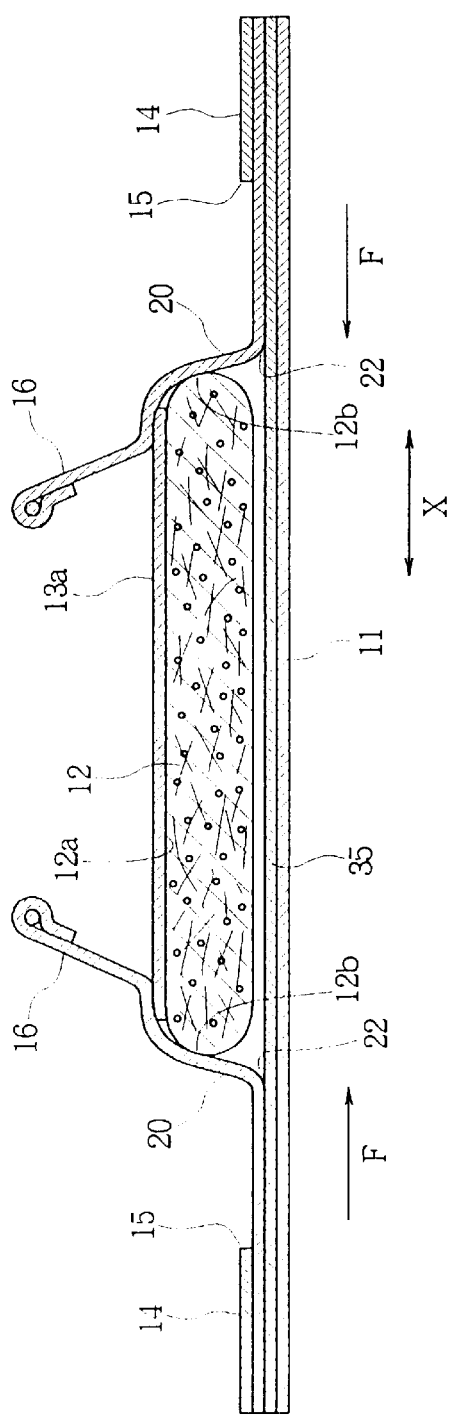
FIG. 8 is a sectional view showing a diaper according to another embodiment of the invention and corresponding to FIG. 4.
Figure 9:
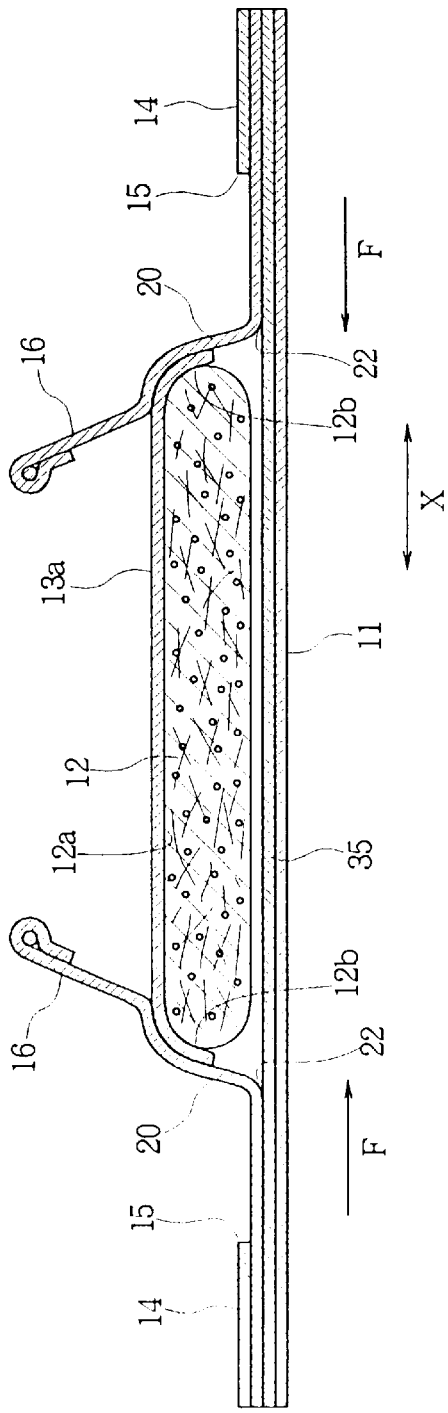
FIG. 9 is a sectional view showing a diaper according to another embodiment of the invention and corresponding to FIG. 4.
Figure 10:
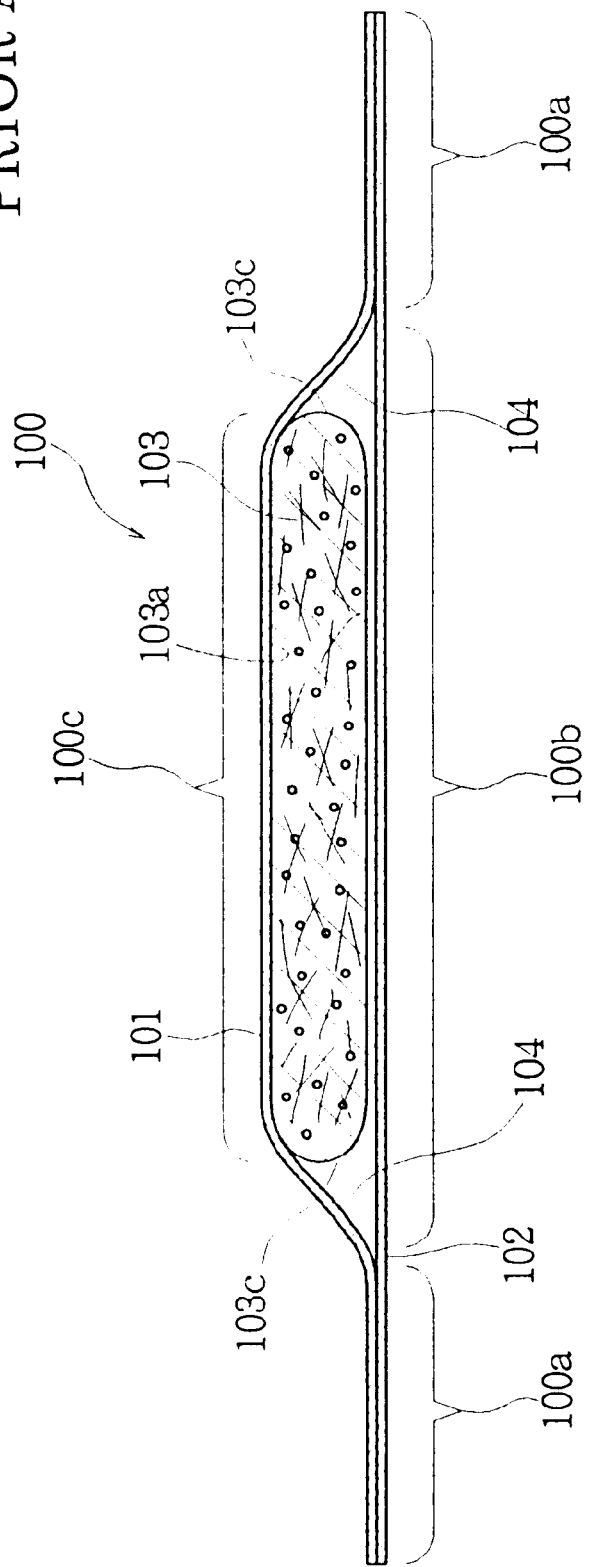
FIG. 10 is a sectional view of a disposable diaper of the related art.

In still another embodiment of the invention shown in FIG. 8, sheets 20 and 20 forming the leakage-preventing cuffs 16 and 16 are jointed to the two sides of the liquid-permeable sheet (or the top sheet) 13a covering the absorbent core 12, while functioning as the aforementioned side sheets. In this case, there is made a structure in which the joint boundaries 22 and 22 between the sheets 20 forming the leakage-preventing cuffs 16 and 16 and the outer sheet 11 enter farther the center side than the two side ends 12b and 12b of the absorbent core 12. In the structure of this case, on the other hand, the sheets forming the aforementioned leakage-preventing cuffs are adhered and jointed to the two side ends 12b and 12b of the absorbent core 12. Alternatively, as shown in FIG. 9, the structure may be modified such that the liquid-permeable sheet (or the top sheet) 13a is adhered and bonded to the two side ends 12b and 12b of the absorbent core 12.

According to the invention, as has been described hereinbefore, the absorbent core is wrapped with the top sheet so that it is hardly twisted, offset or kinked by the motion of the wearer. Especially when the two side ends of the absorbent core 12 are jointed to the top sheet, the absorbent core is reliably held. As a result, either the peeling or the space is hardly established between the top sheet and the absorbent core so that the absorbent core can exhibit the liquid absorbing function sufficiently.

Here, 'comprises/comprising' when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. A disposable diaper having a body including a front face portion to be applied to the abdomen of a wearer; an intermediate portion to be applied to the crotch; and a back face portion to be applied to the back, in which a longitudinal direction is taken from the front face portion to the back face portion of the body, and a transverse direction is taken in a direction perpendicular to the longitudinal direction, comprising:

a top sheet to be directed toward a liquid receiving side; an outer sheet; and an absorbent core sandwiched between the top sheet and the outer sheet, the top sheet being liquid-permeable at least in a portion for covering a transverse center of the absorbent core and being jointed on two transverse sides directly or indirectly to the outer sheet wherein, in a region containing at least a longitudinal center of the intermediate portion, joint boundaries between the top sheet and the outer sheet enter farther the transverse center side than two transverse side ends of the absorbent core.

2. A disposable diaper as set forth in claim 1, wherein the top sheet includes a liquid-permeable sheet and side sheets directly or indirectly jointed to the liquid-permeable sheet on two transverse sides thereof, and wherein joint boundaries between the side sheets and the outer sheet enter farther the transverse center side than the two transverse side ends of the absorbent core.

3. A disposable diaper as set forth in claim 1, wherein in the region containing at least the longitudinal center of the intermediate portion, the top sheet is jointed to the two transverse side ends of the absorbent core.

4. A disposable diaper as set forth in claim 1, wherein in the region containing at least the longitudinal center of the intermediate portion, there is disposed elasticity applying means for bringing the joint boundaries closer to the transverse center.

5. A disposable diaper as set forth in claim 4, wherein the top sheet is not elastically shrunken in the transverse direction, or wherein the transverse elastic shrinking distortion in the free state of the diaper is made larger at the elasticity applying means than at the top sheet.

6. A disposable diaper as set forth in claim 4, wherein the outer sheet is an elastically shrinking sheet for elastically shrinking in the transverse direction, and wherein the elastic shrinking force of the outer sheet is used as the elasticity applying means.

7. A disposable diaper as set forth in claim 4, wherein the elasticity applying means is an elastic member for exhibiting an elastic shrinking force in the transverse direction, and wherein the elastic member is fixed in a transversely extended state either between the absorbent core and the outer sheet or on the outer face of the outer sheet.

8. A disposable diaper as set forth in claim 1, wherein leakage-preventing cuffs are arranged on the liquid receiving side of the body and are extended in the longitudinal direction and spaced apart from each other in the transverse direction, wherein the leakage-preventing cuffs include: sheets having fixed end portions fixed on the diaper along the longitudinal direction and free end portions; and elastic members attached to the sheets at the free end portions or at their vicinities for exhibiting shrinking forces in the longitudinal direction, and wherein in the region containing at least the longitudinal center of the intermediate portion, the fixed end portions of the leakage-preventing cuffs are apart from the two transverse side ends of the absorbent core so that the liquid can be absorbed at the two side ends by the absorbent core.

9. A disposable diaper as set forth in claim 2, wherein leakage-preventing cuffs are arranged on the liquid receiving side of the body and are extended in the longitudinal direction and spaced apart from each other in the transverse direction, wherein the leakage-preventing cuffs include: sheets having fixed end portions fixed on the body along the longitudinal direction and free end portions; and elastic members attached to the sheets at the free end portions or at their vicinities for exhibiting shrinking forces in the longitudinal direction, and wherein the sheets for forming the leakage-preventing cuffs are used as the side sheets.

10. A disposable diaper as set forth in claim 1, wherein two transverse side portions of the front face portion and two transverse side portions of the back face portion are jointed to each other, wherein a waist opening is formed from individual edge portions of the front face portion and the back face portion, and wherein leg openings are formed from two side portions of the intermediate portion so that the body has an underpants shape.

11. A disposable diaper having a body including a front face portion to be applied to the abdomen of a wearer; an intermediate portion to be applied to the crotch; and a back face portion to be applied to the back, in which a longitudinal direction S is taken from the front face portion to the back face portion of the body, and a transverse direction is taken in a direction perpendicular to the longitudinal direction, comprising:

a top sheet to be directed toward a liquid receiving side; an outer sheet; and an absorbent core sandwiched between the top sheet and the outer sheet, the top sheet being liquid-permeable at least in a portion for covering a transverse center of the absorbent core and being jointed on two transverse sides directly or indirectly to the outer sheet wherein, in a region containing at least a longitudinal center of the intermediate portion, there is disposed elasticity applying means for bringing joint boundaries between the top sheet and the outer sheet closer to the transverse center;

wherein the top sheet is not elastically shrunken in the transverse direction, or the transverse elastic shrinking distortion in the free state of the diaper is made larger at the elasticity applying means than at the top sheet; and wherein, in the region containing at least the longitudinal center of the intermediate portion, the top sheet is jointed to two transverse side ends of the absorbent core.

12. A disposable diaper as set forth in claim 11, wherein the top sheet includes a liquid-permeable sheet and side sheets directly or indirectly jointed to the liquid-permeable sheet on two transverse sides thereof, wherein the liquid permeable sheet or the side sheets are not elastically shrunken in the transverse direction, or wherein the transverse elastic shrinking distortion in the free state of the diaper is made larger at the elasticity applying means than at the liquid-permeable sheet or the side sheets, and wherein in the region containing at least the longitudinal center of the intermediate portion, the liquid-permeable sheet or the side sheets are jointed to the two transverse side ends of the absorbent core.

13. A disposable diaper as set forth in claim 11, wherein the outer sheet is an elastically shrinking sheet for elastically shrinking in the transverse direction, and wherein the elastic shrinking force of the outer sheet is used as the elasticity applying means.

14. A disposable diaper as set forth in claim 11, wherein the elasticity applying means is an elastic member for exhibiting an elastic shrinking force in the transverse direction, and wherein the elastic member is fixed in a transversely extended state either between the absorbent core and the outer sheet or on the outer face of the outer sheet.

15. A disposable diaper as set forth in claim 11, wherein leakage-preventing cuffs are arranged on the liquid receiving side of the body and are extended in the longitudinal direction and spaced apart from each other in the transverse direction, wherein the leakage-preventing cuffs include: sheets having fixed end portions fixed on the body along the longitudinal direction and free end portions; and elastic members attached to the sheets at the free end portions or at their vicinities for exhibiting shrinking forces in the longitudinal direction, and wherein in the region containing at least the longitudinal center of the intermediate portion, the fixed end portions of the leakage-preventing cuffs are apart from the two transverse side ends of the absorbent core so that the liquid can be absorbed at the two side ends by the absorbent core.

16. A disposable diaper as set forth in claim 12, wherein leakage-preventing cuffs are arranged on the liquid receiving side of the body and are extended in the longitudinal direction and spaced apart from each other in the transverse direction, wherein the leakage-preventing cuffs include: sheets having fixed end portions fixed on the body along the longitudinal direction and free end portions; and elastic members attached to the sheets at the free end portions or at their vicinities for exhibiting shrinking forces in the longitudinal direction, and wherein the sheets for forming the leakage-preventing cuffs are used as the side sheets.

17. A disposable diaper as set forth in claims 11, wherein two transverse side portions of the front face portion and two transverse side portions of the back face portion are jointed to each other, wherein a waist opening is formed from individual edge portions of the front face portion and the back face portion, and wherein leg openings are formed from two side portions of the intermediate portion so that the body has an underpants shape.

* * * * *